US011243202B2

(12) United States Patent
McPherson et al.

(10) Patent No.: US 11,243,202 B2
(45) Date of Patent: Feb. 8, 2022

(54) METHODS AND COMPOSITIONS FOR DIAGNOSIS AND PROGNOSIS OF RENAL INJURY AND RENAL FAILURE

(71) Applicants: ASTUTE MEDICAL, INC., San Diego, CA (US); UNIVERSITY OF PITTSBURGH—OF THE COMMONWEALTH SYSTEM OF HIGHER EDUCATION, Pittsburgh, PA (US); WESTFÄLISCHE WILHELMS—UNIVERSITÄT MÜNSTER, Münster (DE)

(72) Inventors: Paul McPherson, Encinitas, CA (US); John A. Kellum, Jr., Pittsburgh, PA (US); Alexander Zarbock, Münster (DE)

(73) Assignees: ASTUTE MEDICAL, INC., San Diego, CA (US); UNIVERSITY OF PITTSBURGH—OF THE COMMONWEALTH SYSTEM OF HIGHER EDUCATION, Pittsburgh, PA (US); WESTFÄLISCHE WILHELMS-UNIVERSITÄT MÜNSTER, Münster (DE)

( * ) Notice: Subject to any disclaimer, the term of this patent is extended or adjusted under 35 U.S.C. 154(b) by 1 day.

(21) Appl. No.: 15/565,318

(22) PCT Filed: Apr. 8, 2016

(86) PCT No.: PCT/US2016/026828
§ 371 (c)(1),
(2) Date: Oct. 9, 2017

(87) PCT Pub. No.: WO2016/164854
PCT Pub. Date: Oct. 13, 2016

(65) Prior Publication Data
US 2018/0074054 A1 Mar. 15, 2018

Related U.S. Application Data

(60) Provisional application No. 62/145,442, filed on Apr. 9, 2015.

(51) Int. Cl.
*G01N 33/566* (2006.01)
*G01N 33/68* (2006.01)

(52) U.S. Cl.
CPC ....... *G01N 33/566* (2013.01); *G01N 33/6893* (2013.01); *G01N 2333/4745* (2013.01); *G01N 2333/8146* (2013.01); *G01N 2800/347* (2013.01); *G01N 2800/50* (2013.01)

(58) Field of Classification Search
CPC ... G01N 2333/4745; G01N 2333/8146; G01N 2333/566; G01N 2800/347; G01N 2800/50
See application file for complete search history.

(56) References Cited

U.S. PATENT DOCUMENTS

| | | |
|---|---|---|
| 5,324,634 A | 6/1994 | Zucker |
| 5,480,792 A | 1/1996 | Buechler et al. |
| 5,525,524 A | 6/1996 | Buechler et al. |
| 5,571,698 A | 11/1996 | Ladner et al. |
| 5,631,171 A | 5/1997 | Sandstrom et al. |
| 5,679,526 A | 10/1997 | Buechler et al. |
| 5,824,799 A | 10/1998 | Buechler et al. |
| 5,851,776 A | 12/1998 | Valkirs et al. |
| 5,885,527 A | 3/1999 | Buechler et al. |
| 5,922,615 A | 7/1999 | Nowakowski et al. |
| 5,939,272 A | 8/1999 | Buechler et al. |
| 5,947,124 A | 9/1999 | Buechler et al. |
| 5,955,377 A | 9/1999 | Maul et al. |
| 5,985,579 A | 11/1999 | Buechler et al. |
| 6,019,944 A | 2/2000 | Buechler et al. |
| 6,057,098 A | 5/2000 | Buechler et al. |
| 6,113,855 A | 9/2000 | Buechler et al. |
| 6,140,045 A | 10/2000 | Wohlstadter et al. |
| 6,143,576 A | 11/2000 | Buechler et al. |
| 8,778,615 B2 | 7/2014 | Anderberg et al. |
| 8,993,250 B2 | 3/2015 | Anderberg et al. |
| 9,057,735 B2 | 6/2015 | Anderberg et al. |
| 9,229,010 B2 | 1/2016 | Anderberg et al. |
| 9,360,488 B2 | 6/2016 | Anderberg et al. |
| 9,459,261 B2 | 10/2016 | Anderberg et al. |
| 9,696,322 B2 | 7/2017 | Anderberg et al. |
| 9,784,750 B2 | 10/2017 | Anderberg et al. |

(Continued)

FOREIGN PATENT DOCUMENTS

| | | |
|---|---|---|
| JP | 2003-081838 | 3/2003 |
| WO | WO 2003/054004 | 7/2003 |

(Continued)

OTHER PUBLICATIONS

Meersch et al. Urinary TIMP-2 and IGFBP7 as Early Biomarkers of Acute Kidney Injury and Renal Recovery following Cardiac Surgery. PLoS One, 2014; 9(3):e93460 (Year: 2014).*
Thiele et al. AKI Associated with Cardiac Surgery. Clin J Am Soc Nephrol 10:500-514, 2015 (Year: 2015).*
Yang et al. Remote Ischemic Preconditioning for Prevention of Acute Kidney Injury: A Meta-analysis of Randomized Controlled Trials. Am J Kidney Dis. 64(4):574-583,2014 (Year: 2014).*
Meersch et al. PLoS One, 2014; 9(3):e93460 (Year: 2014).*
Thiele et al. Clin J Am Soc Nephrol 10:500-514, 2015 (Year: 2015).*
Yang et al. Am J Kidney Dis. 64(4):574-583,2014 (Year: 2014).*

(Continued)

*Primary Examiner* — Vanessa L. Ford
*Assistant Examiner* — Sandra E Dillahunt
(74) *Attorney, Agent, or Firm* — Womble Bond Dickinson (US) LLP

(57) ABSTRACT

It is an object of the present invention to provide methods for assessing the efficacy of a remote ischemic preconditioning procedure though the measurement of urinary TIMP-2 and IGFBP7 concentrations.

20 Claims, 2 Drawing Sheets

(56) References Cited

U.S. PATENT DOCUMENTS

| | | |
|---|---|---|
| 9,822,172 B2 | 11/2017 | Vijayendran et al. |
| 9,879,091 B2 | 1/2018 | Vijayendran et al. |
| 10,300,108 B2 | 5/2019 | McPherson et al. |
| 2002/0012906 A1 | 1/2002 | Comper |
| 2003/0186308 A1 | 10/2003 | Young et al. |
| 2004/0023293 A1 | 2/2004 | Kreimer et al. |
| 2004/0126767 A1 | 7/2004 | Anderberg et al. |
| 2004/0253637 A1 | 12/2004 | Buechler |
| 2005/0084880 A1 | 4/2005 | Duman et al. |
| 2006/0240437 A1 | 10/2006 | Krolewski et al. |
| 2006/0257903 A1 | 11/2006 | Akil et al. |
| 2007/0087387 A1 | 4/2007 | Devarajan et al. |
| 2007/0184439 A1 | 8/2007 | Guilford et al. |
| 2007/0248989 A1 | 10/2007 | Devarajan |
| 2007/0249002 A1 | 10/2007 | Hu et al. |
| 2008/0038192 A1 | 2/2008 | Gervais |
| 2008/0133141 A1 | 6/2008 | Frost |
| 2008/0153092 A1 | 6/2008 | Kienle et al. |
| 2008/0254483 A1 | 10/2008 | Darbouret et al. |
| 2009/0130693 A1 | 5/2009 | Bassi et al. |
| 2009/0197287 A1 | 8/2009 | Hu et al. |
| 2009/0220526 A1 | 9/2009 | Hamid |
| 2010/0267061 A1 | 10/2010 | Hsieh et al. |
| 2011/0195429 A1 | 8/2011 | Anderberg et al. |
| 2012/0208717 A1 | 8/2012 | Hu et al. |
| 2012/0283128 A1 | 11/2012 | Anderberg et al. |
| 2013/0157881 A1 | 6/2013 | Anderberg et al. |
| 2014/0213477 A1 | 7/2014 | Anderberg et al. |
| 2014/0323594 A1 | 10/2014 | Anderberg et al. |
| 2014/0343600 A1 | 11/2014 | Leschinsky |
| 2014/0356301 A1 | 12/2014 | Shyur et al. |
| 2014/0377777 A1 | 12/2014 | Anderberg et al. |
| 2016/0146832 A1 | 5/2016 | Chawla et al. |
| 2017/0248613 A1 | 8/2017 | Anderberg et al. |
| 2019/0263926 A1 | 8/2019 | McPherson et al. |

FOREIGN PATENT DOCUMENTS

| | | |
|---|---|---|
| WO | WO 2006/010529 | 2/2006 |
| WO | 2007124331 A2 | 11/2007 |
| WO | WO 2008/067065 | 6/2008 |
| WO | WO 2008/089994 | 7/2008 |
| WO | WO 2009/062520 | 5/2009 |
| WO | WO 2010/025424 | 3/2010 |
| WO | WO 2010/045714 | 4/2010 |
| WO | WO 2010/048346 | 4/2010 |
| WO | WO 2011/017614 | 2/2011 |
| WO | WO 2011/025917 | 3/2011 |
| WO | WO 2011/035323 | 3/2011 |
| WO | WO 2011/075744 | 6/2011 |
| WO | WO 2011/097539 | 8/2011 |
| WO | WO 2011/106746 | 9/2011 |
| WO | WO 2011/162821 | 12/2011 |
| WO | WO 2013/043310 | 3/2013 |
| WO | WO 2013/086359 | 6/2013 |
| WO | WO 2014/070935 | 5/2014 |
| WO | WO 2014/113558 | 7/2014 |
| WO | WO 2014/197729 | 12/2014 |
| WO | WO 2015/021308 | 2/2015 |
| WO | WO 2015/069880 | 5/2015 |
| WO | WO 2015/084939 | 6/2015 |
| WO | WO 2017/060525 | 4/2017 |
| WO | WO 2017/214203 | 12/2017 |
| WO | WO 2018/081578 | 5/2018 |
| WO | WO 2018/145117 | 8/2018 |
| WO | WO 2018/187453 | 10/2018 |

OTHER PUBLICATIONS

Venugopal et al. Effect of Remote Ischemic Preconditioning on Acute Kidney Injury in Nondiabetic Patients Undergoing Coronary Artery Bypass Graft Surgery: A Secondary Analysis of 2 Small Randomized Trials. Am J Kidney Dis 56:1043-1049, 2010 (Year: 2010).*
Venugopal et al. Clinical use of the urine biomarkers [TIMP-2]x[IGFBP-7] for acute kidney injury risk assessment. Am J Kidney Dis 56:1043-1049, 2010 (Year: 2010).*
International Search Report and Written Opinion dated Jul. 8, 2016 in PCT/US2016/026828, Applicant Astute Medical, Inc. (10 pages).
Altom et al., "Optimizing enzyme-linked immunosorbent assays on automated 96-well plate robotic systems," Journal, Laboratory Robotics and Automation, 1990, 2(3):139-46, Abstract only.
Amemiya et al., "Insulin like growth factor binding protein-7 reduces growth of human breast cancer cells and xenografted tumors," Breast Cancer Res Treat, Apr. 2011, 126:373-384.
Aregger et al., "Identification of IGFBP-7 by urinary proteomics as a novel prognostic marker in early acute kidney injury," Kidney International, 2014, 85:909-919.
Bagshaw et al., "A multi-centre evaluation of the RIFLE criteria for early acute kidney injury in critically ill patients," Nephrol Dial Transplant, 2008, 23:1203-1210.
Bagshaw et al., "Urinary biomarkers in septic acute kidney injury," Intensive Care Med, 2007, 33:1285-1296.
Basu et al., "Identification of candidate serum biomarkers for severe septic shock-associated kidney injury via microarray," Crit Care, 2011, 15:R273, 11 pp.
Bellomo et al., "Acute renal failure—definition, outcome measures, animal models, fluid therapy and information technology needs: the Second International Consensus Conference of the Acute Dialysis Quality Initiative (ADQI) Group," Crit Care, 2004, 8:R204-R212.
Bennett et al., "Chronic cyclosporine nephropathy: The Achilles' heel of immunosuppressive therapy," Kidney Int., 1996, 50:1089-1100.
Caron et al.,"Ischemia injury alters endothelial cell properties of kidney cortex: stimulation of MMP-9," Exp Cell Res, 2005, 310:105-116.
Chawla et al., "Identifying critically ill patients at high risk for developing acute renal failure: A pilot study," Kidney Int, 2005, 68:2274-2280.
Chertow et al., "Acute Kidney Injury, Mortality, Length of Stay, and Costs in Hospitalized Patients," J Am Soc Nephrol, 2005, 16(11):3365-3370.
Coca et al., "Biomarkers for the diagnosis and risk stratification of acute kidney injury: A systematic review," Kidney Int, 2008, 73:1008-1016.
Constantin et al., "Plasma neutrophil gelatinase-associated lipocalin is an early marker of acute kidney injury in adult critically ill patients: A prospective study," J Crit Care, 2010, 25(1):176.e1-176.e6.
Cwirla et al., "Peptides on phage: A vast library of peptides for identifying ligands," Proc Natl Acad Sci USA, 1990, 87(16):6378-6382.
Devarajan, "Update on Mechanisms of Ischemic Acute Kidney Injury," J Am Soc Nephrol, 2006, 17(6):1503-1520.
Devlin et al., "Random Peptide Libraries: A Source of Specific Protein Binding Molecules," Science, Jul. 27, 1990, 249(A967):404-406.
El Sabbahy et al., "Ischemic kidney injury and mechanisms of tissue repair," Wiley Interdiscip Rev Syst Biol Med, Sep. 30, 2011, 3(5):606-618.
Fischer et al., "A readers' guide to the interpretation of diagnostic test properties: clinical example of sepsis," Intensive Care Med, 2003, 29:1043-1051.
Fu et al., "Study on the expression of VEGF, MMP-2 and TIMP-2 in the progression of IgA nephropathy," J Clin Exp Pathol, Oct. 24, 2008, 24(5):573-576.
Gocze et al., "Urinary Biomarkers TIMP-2 and IGFBP7 Early Predict Acute Kidney Injury after Major Surgery," PLoS One, Mar. 23, 2015, DOI:10.1371/journal.pone.0120863, pp. 1-11.
Goldstein et al., "Renal Angina," Clin J Am Soc Nephrol, 2010, 5(5):943-949.
Han et al., "Urinary biomarkers in the early diagnosis of acute kidney injury," Kidney Int, 2008, 73(7):863-869.

(56) References Cited

OTHER PUBLICATIONS

Hanley et al., "The Meaning and Use of the Area under a Receiver Operating Characteristic (ROC) Curve," Radiology, Apr. 1982, 143:29-36.
He et al., "A research on serum, urine and tumor tissue hyaluronate assays for detecting malignant ovarian tumors," Zhonghua Fu Chan Ke Za Zhi, Mar. 1995, 30(3):161-163 (abstract only).
Healy et al., "Apoptosis and necrosis: Mechanisms of cell death induced by cyclosporine A in a renal proximal tubular cell line," Kidney Int, 1998, 54:1955-1966.
Hoste et al., "RIFLE criteria for acute kidney injury are associated with hospital mortality in critically ill patients: a cohort analysis.," Crit Care, 2006, 10(3):R73, 10 pp.
Human TIMP-2 ELISA Kit for serum, plasma, cell culture supernatant and urine, RAB0472, Sigma-Aldrich [retrieved from internet on Nov. 13, 2019] <URL:https://www.sigmaaldrich.com/catalog/product/sigma/rab0472?lang=en&region=AU> published Sep. 24, 2012.
Humphreys et al., "Mesenchymal Stem Cells in Acute Kidney Injury," Annu Rev Med., 2008, 59:311-325.
Kamimoto et al., "Hepatocyte growth factor prevents multiple organ injuries in endotoxemic mice through a heme oxygenase-1-dependent mechanism," Biochem Biophys Res Commun, 2009, 380(2):333-337.
Kashani et al., "Discovery and validation of cell cycle arrest biomarkers in human acute kidney injury," Critical Care, 2013, 17(R25):1-12.
Keightley, "A comparison of manual and robotic pipetting for plate-based assays," Laboratory Practice, Journal, 1989, 38(10):53-55—Abstract only.
Kellum, "Acute kidney injury," Crit Care Med, 2008, 36(4):S141-S145.
Kierdorf et al., "Continuous Renal Replacement Therapies Versus Intermittent Hemodialysis in Acute Renal Failure: What Do We Know?," American Journal of Kidney Diseases, Nov. 1996, 28(5)(Sup 3):S90-S96.
Kingsmore et al., "Multiplexed protein profiling on antibody-based microarrays by rolling circle amplification," Current Opin Biotechnol, Feb. 2003, 14(1):74-81.
Kunugi et al., "Inhibition of matrix metalloproteinases reduces ischemia-repertusion acute kidney injury," Lab Invest, 2011, 91(2):170-180.
Kutsukake et al., "Circulating IGF-binding protein 7 (IGFBP7) levels are elevated in patients with endometriosis or undergoing diabetic hemodialysis," Reproductive Biology and Endocrinology, 2008, 6(54):1-6.
Lan, "Clinical significance of determination of serum hyaluronic acid, type III procollagen, collagen IV and laminin in patients with nephropathy," J Guangxi Med Univ., Oct. 2002, 19(5):655-656—incl Engl transl of abstract only.
Lassnigg et al., "Minimal Changes of Serum Creatinine Predict Prognosis in Patients after Cardiothoracic Surgery: A Prospective Cohort Study," J Am Soc Nephrol, 2004, 15(6):1597-1605.
López-Bermejo et al., "Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues," J Clin Endocrinol Metab, Jul. 2003, 88(7):3401-3408.
MacCallum et al., "Antibody-antigen Interactions: Contact Analysis and Binding Site Topography," J Mol Biol, 1996, 262:732-745.
Matousovic et al., "IgA-containing immune complexes in the urine of IgA nephropathy patients," Nephrol Dial Transplant, Sep. 2006, 21(9):2478-2484.
Mazanowska et al., "Imbalance of Metalloproteinase/Tissue Inhibitors of Metalloproteinase System in Renal Transplant Recipients With Chronic Allograft Injury," Transplant Proc, 2011, 43:3000-3003.
McCullough et al., "Contrast-Induced Nephropathy (CIN) Consensus Working Panel: Executive Summary," Rev Cardiovasc Med, 2006, 7(4):177-197.

Mehran et al., "A Simple Risk Score for Prediction of Contrast-Induced Nephropathy After Percutaneous Coronary Intervention: Development and Initial Validation," J Am Coll Cardiol, 2004, 44(7):1393-1399.
Mehta et al., "Acute Kidney Injury Network: report of an initiative to improve outcomes in acute kidney injury," Crit Care, 2007, 11(2):R31, 8 pp.
Nejat et al., "Urinary cystatin C is diagnostic of acute kidney injury and sepsis, and predicts mortality in the intensive care unit," Critical Care, 2010, 14(3):R85, 13 pp.
Nelson et al., "A computer program for calculating antibody affinity constants," Comput Methods Programs Biomed, 1988, 27(1):65-68.
Pajenda et al., "NephroCheck data compared to serum creatinine in various clinical settings," BMC Nephrology, 2015, 16:206, 7 pp.
Parikh et al., "New biomarkers of acute kidney injury," Crit Care Med, 2008, 36(4 Suppl):S159-S165.
Paul, "Fundamental Immunology," Third Edition, Structure and Function of Immunoglobulins, 1993, 8:292-295.
Praught et al., "Are small changes in serum creatinine an important risk factor?," Curr Opin Nephrol Hypertens, 2005, 14(3):265-270.
Ricci et al., "The RIFLE criteria and mortality in acute kidney injury: A systematic review," Kidney Int, 2008, 73(5):538-546.
Scott et al., "Searching for Peptide Ligands with an Epitope Library," Science, Jul. 27, 1990, 249:386-390.
Shek et al., "Robotic enzyme-linked immunosorbent assay (ELISA) system for rodent serology: modifications to enhance capacity, throughput and sensitivity," Proc Int Symp Lab Autom Rob, Conference 1992, pp. 282-298—Abstract only.
Siew et al., "Biological Markers of Acute Kidney Injury," J Am Soc Nephrol, 2011, 22:810-820.
Stampfer et al., "Risk Factor Criteria," Circulation, 2004, 109(Suppl IV):IV-3-IV-5.
Stenvinkel et al., "High Serum Hyaluronan Indicates Poor Survival in Renal Replacement Therapy," Am J Kidney Dis, Dec. 1999, 34(6):1083-1088.
Su et al., "Diagnostic value of urine sTREM-1 for sepsis and relevant acute kidney injuries: a prospective study," Crit Care, 2011, 15:R250, 10 pp.
Tan et al., "The level of urinary secretory immunoglobulin A (sIgA) of patients with IgA nephropathy is elevated and associated with pathological phenotypes," Clin Exp Immunol, Apr. 2009, 156(1):111-116.
Thakar et al., "A Clinical Score to Predict Acute Renal Failure after Cardiac Surgery," J Am Soc Nephrol, 2005, 16:162-168.
Vajdos et al., "Comprehensive Functional Maps of the Antigen-binding Site of an Anti-ErbB2 Antibody Obtained with Shotgun Scanning Mutagenesis," J Mol Biol, 2002, 320:415-428.
Van Erp et al., "Application of a Sol Particle Immunoassay to the Determination of Affinity Constants of Monoclonal Antibodies," J Immunoassay, 1991, 12(3):425-443.
Waikar et al., "Imperfect Gold Standards for Kidney Injury Biomarker Evaluation," J Am Soc Nephrol, Jan. 2012, 23(1):13-21.
Ward et al., "Binding activities of a repertoire of single immunoglobulin variable domains secreted from *Escherichia coli*," Nature, Oct. 12, 1989, 341:544-546.
Wen et al., "One dose of cyclosporine A is protective at initiation of folic acid-induced acute kidney injury in mice," Nephrol Dial Transplant, 2012, 27:3100-3109.
Wijeysundera et al., "Derivation and Validation of a Simplified Predictive Index for Renal Replacement Therapy After Cardiac Surgery," JAMA, Apr. 25, 2007, 297:1801-1809.
Wiki: "Chronic kidney disease," Jan. 3, 2020, Retrieved from the internet: URL:https://en.wikipedia.org/wiki?Chronic_kidney_disease [retrieved on Jan. 7, 2020].
Wilson et al., "Simplified conjugation chemistry for coupling peptides to F(ab') fragments: autologous red cell agglutination assay for HIV-1 antibodies," J Immunol Methods, 1994, 175:267-273.
Yan et al., "Expression of MMP-2 and TIMP-1 in renal tissue of patients with chronic active antibody-mediated renal graft rejection," Diagn Pathol, Oct. 12, 2012;7:141.
Yarmush et al., "Coupling of antibody-binding fragments to solid-phase supports: site-directed binding of F(ab')2 fragments," J Biochem Biophys Methods, 1992, 25:285-297.

(56) References Cited

OTHER PUBLICATIONS

Yasuda et al., "Insulin like growth factor-1 increases p21 expression and attenuates cisplatin-induced acute renal injury in rats," Clin Exp Nephrol, 2004, 8:27-35.

Yasuda et al., "Simvastatin improves sepsis-induced mortality and acute kidney injury via renal vascular effects," Kidney Int, May 2006, 69(9):1535-1542.

Zhang et al., "The level of serum secretory IgA of patients with IgA nephropathy is elevated and associated with pathological phenotypes," Nephrol Dial Transplant, Jan. 2008, 23(1):207-212.

Chindarkar et al., "Reference intervals of urinary acute kidney injury (AKI) markers [IGFBP7]•[TIMP2] in apparently healthy subjects and chronic comorbid subjects without AKI," Clinica Chimica Acta, 2016, 452:32-37.

Hoste et al., "Derivation and validation of cutoffs for clinical use of cell cycle arrest biomarkers," Nephrol Dial Transplant, 2014, 29:2054-2061.

Klein et al., "Renal replacement therapy in acute kidney injury," Medizinische Klinik, Urban & Vogel, Munich, May 2, 2017, 112(5):437-443 (in German, includes English abstract on p. 439).

Ostermann et al., "Patient Selection and Timing of Continuous Renal Replacement Therapy," Blood Purif, 2016, 42:224-237.

Pilarczyk et al., "Tissue inhibitor of metalloproteinase 2 and insulin-like growth factor-binding protein 7, New biomarker combination for early recognition of acute kidney injury in cardiac surgery" Zeitschrift fur Herz-, Thorax- and Gefaesschirurgie, Mar. 1, 2017, 31:190-199 (in German, includes English abstract on p. 192).

Vijayan et al., "Clinical Use of the Urine Biomarker [TIMP-2] x [IGFBP7] for Acute Kidney Injury Risk Assessment," Am J Kidney Dis, 2016, 68(1):19-28.

Wasung et al., "Biomarkers of renal function, which and when?," Clinica Chimica Acta, 2015, 438:350-357.

Extended European Search Report dated Dec. 3, 2020, in European application (No. 18797960.4).

Official action dated Mar. 27, 2020, in European application (No. 16777449.6).

Wetz et al., "Quantification of urinary TIMP-2 and IGFBP-7: an adequate diagnostic test to predict acute kidney injury after cardiac surgery?," Critical Care, 2015, 19(1):3.

Extended European Search Report dated Oct. 19, 2018, in European application No. 16777449.6.

* cited by examiner

METHODS AND COMPOSITIONS FOR DIAGNOSIS AND PROGNOSIS OF RENAL INJURY AND RENAL FAILURE

CROSS-REFERENCE TO RELATED APPLICATIONS

The present invention is filed under 35 U.S.C. § 371 as the U.S. national phase of International Patent Application No. PCT/US2016/026828, filed Apr. 8, 2016, which designated the United States and claims priority to U.S. Provisional Patent Application No. 62/145,442, filed Apr. 9, 2015, which is hereby incorporated by reference in its entirety.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17$^{th}$ Ed., McGraw Hill, N.Y., pages 1741-1830, which are hereby incorporated by reference in their entirety. Renal disease and/or injury may be acute or chronic. Acute and chronic kidney disease are described as follows (from Current Medical Diagnosis & Treatment 2008, 47$^{th}$ Ed, McGraw Hill, N.Y., pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17$^{th}$ ed., Chapter 222, and which is hereby incorporated by reference in their entirety:

| Type | Risk Factors |
|---|---|
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, *J Am Soc Nephrol* 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And Included Two Clinical Outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Ischemic preconditioning (also known as "remote ischemic preconditioning" or "RIPC") is a phenomenon whereby brief episodes of ischemia-reperfusion applied in distant tissues or organs render the myocardium resistant to a subsequent sustained episode of ischemia. RIPC has been observed in several animal species. The chain of events which confers resistance to ischemia is only partially understood. It is now well established that the protective effects of preconditioning are transient and last for <2 hours. However, a "second window" of delayed ischemic preconditioning has been observed in different species, occurring 24 hours after the preconditioning stimulus and lasting for about 48 hours. This has led to a theory that RIPC includes the activation of genes encoding for cytoprotective proteins, such as heat shock proteins or antioxidant enzymes. RIPC may attenuate renal injury by releasing various molecules such as damage-associated molecular patterns (DAMPS) that are then filtered by the kidney and signal through Toll-like receptors in the proximal tubule epithelia. This signaling may then induce natural defenses such as bioenergetic down-regulation and temporary cell-cycle arrest. These defenses, once engaged, can then protect the kidney during subsequent inflammatory or ischemic stress.

There have been some efforts to traslate the concept of RIPC to patients undergoing planned ischemic events such as abdominal aortic aneurysm repair, angioplasty, and coronary artery bypass graft surgery. Zimmerman et al., Kidney Intl. 80: 861-67, 2011, reported that RIPC induced by application of an automated thigh tourniquet to produce three 5-min intervals of lower extremity ischemia separated by 5-min intervals of reperfusion significantly reduced acute kidney injury in patients undergoing cardiopulmonary bypass-assisted cardiac surgery. However, randomised trials investigating the effect of RIPC on AKI after cardiac surgery have shown conflicting results. Li et al., J. Cardiothoracic Surg. 8: 43 (doi: 10.1186/1749-8090-8-43) reported from a meta analysis of available publications that RIPC did not produce a difference in the levels of renal biomarkers, incidence of renal replacement therapy, mortality, hospital stay, or intensive care unit stay related to the development of AKI during cardiac and vascular interventions.

(AKI) remains a vexing clinical problem, in part, because it is difficult to identify before there is loss of organ function, which may then become irreversible. Moreover, available therapies are mainly predicated on supportive measures and the removal of nephrotoxic agents. These limitations underscore the need for better methods to detect, assess, and treat AKI, preferably before irreversible injury has occurred.

BRIEF SUMMARY OF THE INVENTION

It is an object of the present invention to provide methods and compositions for assessing risk of an acute kidney injury occurring following administration of a therapeutic intervention on a patient known to increase risk of an AKI prior to performing that therapeutic intervention. It is another object of the invention to provide methods of performing ischemic preconditioning on a patient in need thereof. In general, these methods comprise performing a remote ischemic preconditioning procedure on the patient prior to performing the therapeutic intervention;

obtaining a urine sample from the patient following the remote ischemic preconditioning procedure and prior to performing the therapeutic intervention;

performing a first assay which measures Insulin-like growth factor-binding protein 7 to provide a first assay result, and a second assay which measures metallopeptidase inhibitor 2 to provide a second assay result; and using the first and second assay results to assess the effectiveness of the remote ischemic preconditioning procedure to reduce the patient's risk of AKI that results from the therapeutic intervention.

As described hereinafter, these biomarkers can be used to assess the current cell cycle state of the kidney, and as a result may be used to assess the protective effect of the RIPC procedure. In certain aspects, the first and second assay results are combined into a single composite value that is a function of the first and second assay results. This composite result may be correlated to a likelihood that the subject is at risk of an acute renal injury following the therapeutic intervention.

By way of example, this correlation may comprise comparing the single composite value to a threshold, wherein when the single composite value is below the threshold, the patient is at an increased risk of acute renal injury resulting from the therapeutic intervention relative to a risk when the single composite value is above the threshold. As described herein, such a threshold may be obtained from a population study, or from an earlier value from the same individual (e.g., from a time preceding the RIPC procedure.

In various embodiments, the contemplated therapeutic intervention which is preceded by the RIPC procedure is selected from the group consisting of administration of one or more nephrotoxic agents (e.g., radiocontrast agents, antibiotics with nephrotoxic potential, heavy metal preparations, cancer chemotherapeutic agents, nonsteroidal anti-inflammatory drugs [NSAIDs], tacrolimus, aminoglycosides, foscarnet, ethylene glycol, hemoglobin, myoglobin, ifosfamide, methotrexate, streptozotocin etc.), and performance of one or more surgical interventions (e.g., heart valve repair/replacement, percutaneous coronary intervention (PCI), coronary artery bypass grafting, aneurysm repair, endovascular stent repair, other cardiac surgery, etc.).

Various methods may be used to induce RIPC in the subject. By way of example, RIPC may be accomplished by performing cycles of ischemia/reperfusion (e.g., 4 cycles of alternating 5-minute inflation to the individual's systolic blood pressure plus 50 mm Hg and 5-minute deflation) using a standard upper-arm blood pressure cuff to induce transient and repetitive arm ischemia and reperfusion. Alternatively, a thigh tourniquet may be tightened and loosened to produce cycles (e.g., three 5-min intervals separated by 5-min intervals of reperfusion) of repetitive lower extremity ischemia/reperfusion. Examples of systems for producing RIPC are disclosed in, for example, U.S. Pat. No. 8,790,266. Other methods of inducing RIPC include exercise-induced ischemia and pharmacological preconditioning (e.g., by administering volatile anesthetics (e.g., sevoflurane), propofol, verapamil or nicorandil and adenosine). This list is not meant to be limiting.

Additional clinical indicia of health status, and particularly of renal sufficiency, may be combined with the IGFBP7 and/or TIMP-2 measurements in the methods described herein. Such clinical indicia may include one or more of: a baseline urine output value for the patient, a baseline change in serum creatinine for the patient, demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), other clinical variables (e.g., blood pressure, temperature, respiration rate), risk scores (APACHE score, PREDICT score, TIMI Risk Score for UA/NSTEMI, Framingham Risk Score, risk scores of Thakar et al. (J. Am. Soc. Nephrol. 16: 162-68, 2005), Mehran et al. (J. Am. Coll. Cardiol. 44: 1393-99, 2004), Wijeysundera et al. (JAMA 297: 1801-9, 2007), Goldstein and Chawla (Clin. J. Am. Soc. Nephrol. 5: 943-49, 2010), or Chawla et al. (Kidney Intl. 68: 2274-80, 2005)), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with IGFBP7 and/or TIMP-2 assay result(s) are described hereinafter and in Harrison's Principles of Internal Medicine, 17th Ed., McGraw Hill, N.Y., pages 1741-1830, and Current Medical Diagnosis & Treatment 2008, 47th Ed, McGraw Hill, N.Y., pages 785-815, each of which are hereby incorporated by reference in their entirety.

Various methods may be used to evaluate the IGFBP7 and/or TIMP-2 biomarker results. By way of example, a decision threshold (or "cutoff") for a biomarker or a combination of biomarkers may be selected which has been predetermined to divide a relevant population into two or more groups. A first group, often called the "nondiseased" population for convenience, represents those patients which have a high risk of AKI. A second group represents those patients with a risk of AKI is small as measured by the biomarker result. A relative risk of AKI for the second group is determined relative to the risk in the first group. A relative risk of 1 means there is no difference in risk between the two groups; while a relative risk of >1 means the risk is higher in the second group.

In an alternative, one may look for a change in the IGFBP7 and/or TIMP-2 biomarker results resulting from the TIPC procedure by comparing biomarker results pre-RIPC and post-RIPC. By way of example, if the IGFBP7 and/or TIMP-2 biomarker results show an increase resulting from the RIPC procedure, a decreased risk of acute renal injury resulting from the therapeutic intervention is indicated relative to a risk when IGFBP7 and/or TIMP-2 biomarker results are unchanged or reduced. In the latter case, this may indicate that the RIPC procedure was ineffective, so the therapeutic intervention may be postponed. Alternatively, a second RIPC procedure may be attempted, and IGFBP7 and/or TIMP-2 biomarker results obtained again following the second RIPC procedure in order to determine its effectiveness.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured IGFBP7 and/or TIMP-2 concentrations may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the value recited herein refers to +/−5% of a given value.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

DETAILED DESCRIPTION OF THE INVENTION

Figure 1:
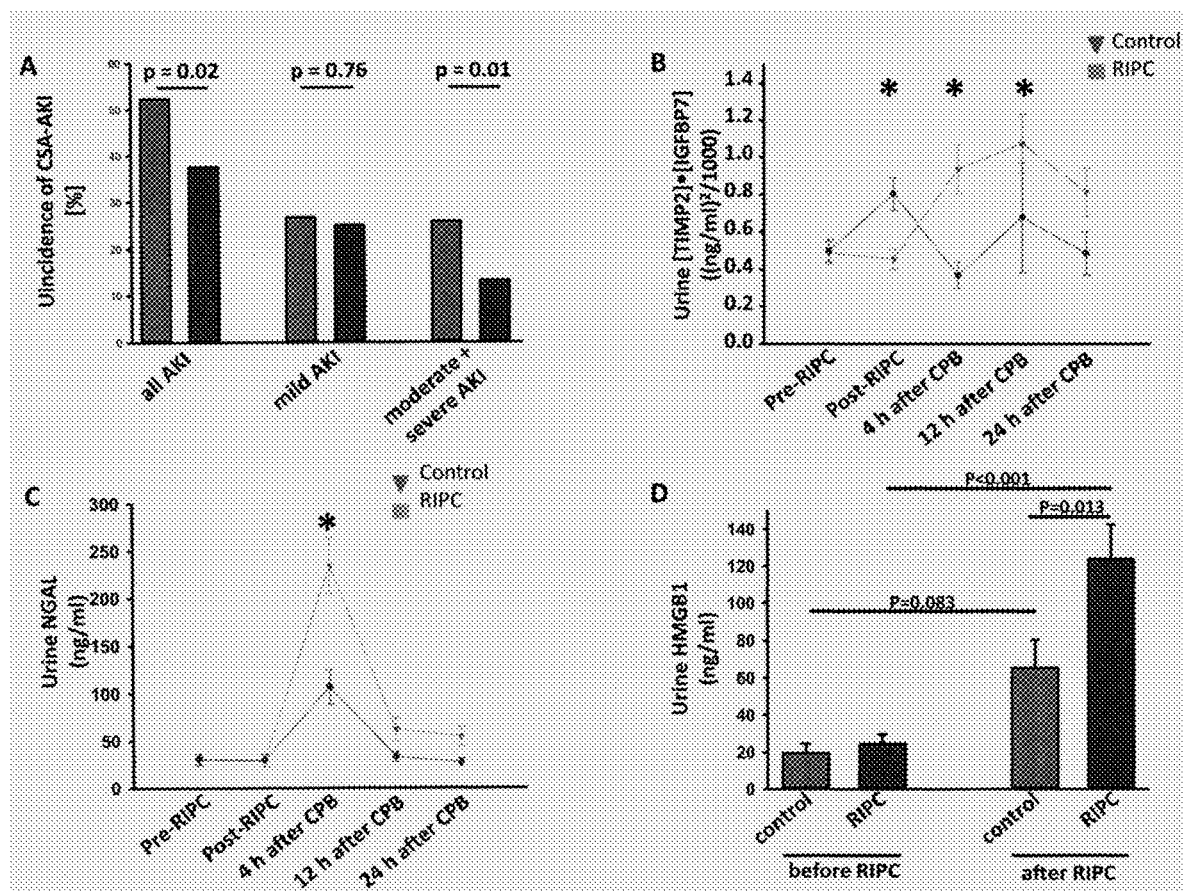
FIG. 1 depicts (A) rate of acute kidney injury in cardiac surgery patients with remote ischemic preconditioning (RIPC) and control patients; (B) mean urine [TIMP-2]·[IGFBP7] concentrations before and after remote ischemic preconditioning (RIPC) and cardiopulmonary bypass; (C) mean NGAL concentrations before and after remote ischemic preconditioning (RIPC) and cardiopulmonary bypass; and (D) mean HMGB-1 concentrations before and after remote ischemic preconditioning (RIPC) and cardiopulmonary bypass. Error bars are SE. Asterisks (*) denote significant differences (p≤0.05) between groups (control, RIPC) at the respective time point. CPB, cardiopulmonary bypass.

Acute kidney injury (AKI) is defined as an abrupt or rapid decline in renal filtration function, and is a clinical syndrome that is associated with significant morbidity and mortality. The incidence of AKI has more than doubled in the past decade and is projected to continue to increase. Patients with AKI are cared for by a multitude of specialists including, but not limited to, emergency medicine physicians, internists, pediatricians, surgeons, intensivists, and nephrologists. Patients who develop AKI often require renal replacement therapy (RRT), but clinicians often disagree about the optimal timing of the initiation of RRT.

Rather than performing a therapeutic intervention, and then dealing with the consequences of a resulting AKI, it would be preferable to perform some prophylactic procedure in advance of the therapeutic intervention. RIPC describes the phenomenon in which transient nonlethal ischemia and reperfusion applied to an organ or tissue protects another organ or tissue from a subsequent injury due to some insult, such as surgery or administration of a toxic compound. However, as discussed in Pei et al., PLoS ONE 9(12): e1 115500 (doi:10.1371/journal.pone.0115500), results of RIPC can be inconsistent. The present invention provides methods in which biomarkers can be used to assess the current renal status in subjects and the success (or lack thereof) of a RIPC procedure being performed.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter.

As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL (≥8.8 kmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl (≥26.4 μmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

The term "subject" as used herein refers to a human or non-human organism. Thus, the methods and compositions described herein are applicable to both human and veterinary disease. Further, while a subject is preferably a living organism, the invention described herein may be used in post-mortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

In general, immunoassays are specific binding assay that involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Such assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of solid phases and detectable label conjugates often comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of IGFBP7 and/or TIMP-2. The kit comprises reagents for the analysis of at least one test sample which comprise at least one antibody that bind each biomarker being assayed. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7$ $M^{-1}$, and preferably between about $10^8$ $M^{-1}$ to about $10^9$ $M^{-1}$, about $10^9$ $M^{-1}$ to about $10^{10}$ $M^{-1}$, or about $10^{10}$ $M^{-1}$ to about $10^{12}$ $M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

While the present application describes antibody-based binding assays in detail, alternatives to antibodies as binding species in assays are well known in the art. These include receptors for a particular target, aptamers, etc. Aptamers are oligonucleic acid or peptide molecules that bind to a specific target molecule. Aptamers are usually created by selecting them from a large random sequence pool, but natural aptamers also exist. High-affinity aptamers containing modified nucleotides conferring improved characteristics on the ligand, such as improved in vivo stability or improved delivery characteristics. Examples of such modifications include chemical substitutions at the ribose and/or phosphate and/or base positions, and may include amino acid side chain functionalities.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the 97.5th percentile of the concentration seen in a normal population. Another method may be to look at serial samples from the same patient, where a prior "baseline" result is used to monitor for temporal changes in a biomarker level.

Population studies may also be used to select a decision threshold. Reciever Operating Characteristic ("ROC") arose from the field of signal dectection therory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1−specificity, the ROC graph is sometimes called the sensitivity vs (1−specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1-specificity)) of greater than 1, at least 2, more preferably at least 3, still more preferably at least 5, and most preferably at least 10; and or a negative likelihood ratio (calculated as (1-sensitivity)/specificity) of less than 1, less than or equal to 0.5, more preferably less than or equal to 0.3, and most preferably less than or equal to 0.1

Clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined in the methods of the present invention are described hereinafter and in Harrison's Principles of Internal Medicine, 17$^{th}$ Ed., McGraw Hill, N.Y., pages 1741-1830, and Current Medical Diagnosis & Treatment 2008, 47$^{th}$ Ed, McGraw Hill, N.Y., pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m$^2$ can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr\text{-corrected}} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., *Nephrol. Dial. Transplant.* 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N J, 1999. In addition, since the methods and compositions described herein provide prognostic information, the markers of the present invention may be used to monitor a course of treatment. For example, improved or worsened prognostic state may indicate that a particular treatment is or is not efficacious.

The distinction between prerenal AKI and instrinsic AKI is an important clinical assessment that directs the therapeutic intervention(s). Patients who are prerenal need therapies directed at hemodynamics to improve renal blood flow. These therapies are often involve inotropes, intravenous fluids and/or vasopressors. Each of these interventions have potential side effects (e.g. arrhythmias, volume overload, vasoconstriction) and would not be advisable to implement these therapies if they are not destined to improve renal function. Thus, the distinction between prerenal AKI and intrinsic AKI helps determine the therapy which should be prescribed. If prerenal AKI is not present, therapy is directed at mitigating AKI and providing supportive care.

Prerenal acute renal failure occurs when a sudden reduction in blood flow to the kidney camera (renal hypoperfusion) causes a loss of kidney function. Causes can include low blood volume, low blood pressure, shunting of blood from the kidney, heart failure, and local changes to the blood vessels supplying the kidney. In prerenal acute renal failure, there is nothing wrong with the kidney itself. Treatment focuses on correcting the cause of the prerenal acute renal failure.

In prerenal AKI without fluid overload, administration of intravenous fluids is typically the first step to improve renal function. This is particularly used in patients in whom prerenal AKI develops as the result of intravascular volume depletion in order to restore normal circulating blood volume. Volume status may be monitored to avoid over- or under-replacement of fluid as described herein. Fluids with colloidal particles such as albumin may be preferred over simple saline infusion. In a prerenal condition wherein the forward flow is compromised, drugs directed at augmenting cardiac output are typically employed.

In patients with congestive heart failure in whom AKI has developed as a result of excessive diuresis, withholding of diuretics and cautious volume replacement may be sufficient to restore kidney function. Inotropes such as norepinephrine and dobutamine may be given to improve cardiac output and hence renal perfusion.

Hospitalized fluid overload patients are typically treated with fluid restriction, IV diuretics, inotropes (e.g., milrinone or dobutamine) and combination therapies. The loop diuretic furosemide is the most frequently prescribed diuretic for treatment of volume overload in HF. Initial oral doses of 20 to 40 mg once a day should be administered to patients with dyspnea on exertion and signs of volume overload who do not have indications for acute hospitalization. Severe overload and pulmonary edema are indications for hospitalization and intravenous furosemide. Some patients with mild HF can be treated effectively with thiazide diuretics. Those who have persistent volume overload on a thiazide diuretic should be switched to an oral loop diuretic. In patients with severe kidney injury, diuretics may not result in significant diuresis. Ultrafiltration, also called aquapheresis, may be used to treat fluid overload in such cases.

In contrast to prerenal AKI, the main goal of treatment of acute tubular necrosis (ATN) is to prevent further injury to the kidney. Ischemic ATN can be caused when the kidneys are not sufficiently perfused for a long period of time (e.g. due to renal artery stenosis) or by shock. Sepsis causes 30% to 70% of deaths in patients with ATN; therefore, avoidance of intravenous lines, bladder catheters, and respirators is recommended. Because septic patients are vasodilated, large volumes of administered fluid accumulate in the lung interstitium of these patients. Extracellular fluid volume should be assessed promptly, and repletion of any deficit should be initiated promptly. Hemodynamic status should be modified by appropriate fluid therapy, giving vasopressors and/or inotropes and treating any underlying sepsis. All possible nephrotoxic drugs should be stopped. In addition, doses of all medications that are eliminated by the kidney should be adjusted.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1: Study Design and Participants

After obtaining approval from the institutional review boards at each site, a prospective, multi-center, double-blind, randomized, controlled trial was undertaken. Consecutive patients were approached for enrollment during preadmission consultations and provided written informed consent. The study was conducted according to the principles of the Declaration of Helsinki. Eligible patients were adults at high risk for AKI who underwent cardiac surgery with the use of cardiopulmonary bypass (CPB) at the Universities of Münster, Tübingen, Freiburg or Bochum (Germany), between August 2013 and June 2014. A Cleveland Clinic Foundation score of 6 or more was used to define patients at high risk for AKI. The score is composed of different risk factors, including patient characteristics, co-morbidities, and type of surgery. Exclusion criteria were acute myocardial infarction up to 7 days before surgery, age <18 years, off-pump heart surgery, pre-existing AKI, kidney transplantation, chronic kidney disease with a glomerular filtration rate (GFR)<30 ml/min., pregnancy, peripheral vascular disease affecting the upper limbs, hepatorenal syndrome, and drug therapy with sulfonamide or nicorandil (preconditioning-blocking and preconditioning-mimetic medication, respectively).

Of 790 patients screened for the trial, 240 patients were enrolled and randomized to either RIPC (n=120) or sham-RIPC (n=120) and included in the primary analysis. The baseline and intraoperative characteristics did not differ between groups (Table 1).

TABLE 1

Baseline and operative characteristics*

|  | Control (n = 120) | RIPC (n = 120) |
|---|---|---|
| Age | 73 (10) | 73 (9) |
| Gender |  |  |
| Male [%] | 75 (62.5) | 76 (63.3) |
| Female [%] | 45 (37.5) | 44 (36.7) |
| ASA |  |  |
| 1 | 0 (0) | 0 (0) |
| 2 | 24 (20.0) | 27 (22.5) |
| 3 | 88 (73.3) | 86 (71.7) |
| 4 | 8 (6.7) | 7 (5.8) |
| Preoperative creatinine [mg/dl] | 1.10 (0.42) | 1.10 (0.37) |
| eGFR [ml/min per 1.73 m$^2$] | 60 (16) | 60 (13) |
| Comorbidities |  |  |
| Hypertension [%] | 116 (96.7) | 116 (96.7) |
| Congestive Heart Failure [%] | 101 (84.2) | 101 (84.2) |
| Diabetes [%] | 44 (36.7) | 46 (38.3) |
| COPD [%] | 40 (33.3) | 36 (30.0) |
| Chronic kidney disease [%] | 39 (32.5) | 35 (29.2) |
| Previous heart surgery [%] | 14 (11.7) | 13 (10.8) |
| Left ventricular EF < 35% [%] | 13 (10.8) | 23 (19.2) |
| Medication [%] |  |  |
| Aspirin | 66 (55.0) | 77 (64.2) |
| Clopidogrel | 15 (12.5) | 11 (9.2) |
| β blockers | 78 (65.0) | 68 (56.7) |

TABLE 1-continued

Baseline and operative characteristics*

|  | Control (n = 120) | RIPC (n = 120) |
|---|---|---|
| Statins | 85 (70.8) | 80 (66.7) |
| Diuretics | 71 (59.2) | 63 (52.5) |
| ACE inhibitors or ARBs | 73 (60.8) | 71 (59.2) |
| Intraoperative characteristics |  |  |
| Aortic cross-clamp duration [min] | 78 (42) | 86 (37) |
| Cardiopulmonary bypass time [min] | 116 (78) | 120 (56) |
| Procedure |  |  |
| CABG only [%] | 36 (30.0) | 44 (36.7) |
| Valve only [%] | 21 (17.5) | 28 (23.3) |
| Combined or other [%] | 63 (52.5) | 48 (40.0) |

*Data are mean (SD) or number (%). There were no significant differences in baseline and operative characteristics between the groups (P values range from 0.06 to 1.00)
RIPC, remote ischemic preconditioning; ASA,; eGFR, estimated glomerular filtration rate; COPD, chronic obstructive pulmonary disease; EF, ejection fraction; CABG, coronary artery bypass graft.

Patients were randomized on a 1:1 basis stratified by center. Randomization codes were computer generated and kept in sealed envelopes. On the day of surgery, patients were assigned to undergo either RIPC or sham-RIPC (control). A staff anesthetist not involved in the study or analysis opened the envelope in the preparation room where anesthesia was induced. Patients, cardiac surgeons, and intensive care physicians were unaware of treatment assignment.

Example 2: Procedures

Anaesthesia was induced according to the standard of care at each center and maintained with volatile anesthetics, because propofol may interfere with RIPC. The management of CPB was performed as follows: the mean arterial blood pressure of 60-70 mmHg, the use of non-pulsatile CPB, α-stat acid-base management to regulate carbon dioxide tension, haematocrit values 25-30%, blood glucose levels <200 mg/dL, and the use of arterial line filters.

After induction of anesthesia and before skin incision RIPC was performed. This consisted of three cycles of 5 min inflation of a blood-pressure cuff to 200 mm Hg (or at least to a pressure 50 mmHg higher than the systolic arterial pressure) to the left upper arm followed by 5 min reperfusion with the cuff deflated. In patients assigned to the control group, sham-RIPC intervention was induced by three cycles of right upper limb 'pseudo'-ischemia (low pressure: 5 min blood-pressure cuff inflation to a pressure of 20 mm Hg and 5-min cuff deflation). The surgical procedure and perioperative care were performed according to the standard at each center.

Example 3: Outcomes

The primary endpoint was the occurrence of AKI within the first 72 hrs after surgery. AKI was defined according to the KDIGO criteria. Secondary endpoints were severe AKI (stage 2-3) within 72 hrs, 30-day all-cause mortality, need for renal replacement therapy (RRT) during index hospitalization, duration of ventilator support, length of stay in the intensive care unit (ICU), length of hospital stay, concentrations of various urinary biomarkers in the first 24 hours after surgery, and perioperative myocardial infarction and stroke during the index hospital stay.

Clinical variables were abstracted from the medical record. Initiation of renal replacement therapy (RRT) was at the discretion of the ICU clinicians blinded to treatment assignment. Criteria for RRT were not included in the protocol. Perioperative myocardial infarction and stroke were defined as described in the art.

Example 4: Blood and Urine Sampling and Analysis

Blood samples were drawn before surgery and at pre-specified time points after surgery for measurement of serum creatinine concentrations. Estimated glomerular filtration rate was obtained with the modification of diet in renal disease formula. Urine samples for biomarkers were collected before RIPC/sham-RIPC, after inducing RIPC or sham-RIPC, and at 4, 12, and 24 h after surgery. The product of urine tissue inhibitor of metalloproteinases-2 (TIMP-2) and insulin-like growth factor-binding protein 7 (IGFBP7) concentrations, referred to herein as [TIMP-2]·[IGFBP7], was measured with the NephroCheck™ Test (Astute Medical, San Diego, Calif., USA). Urine neutrophil gelatinase-associated lipocalin (NGAL), was measured with a commercially available assay (Dianova, Hamburg, Germany) according to the manufacturer's protocol. Urine high mobility group box (HMGB)-1 was measured with a commercially available assay (antibodies-online.com, Germany) according to the manufacturer's protocol.

Example 5: Statistical Analysis

A necessary sample size was based on the primary endpoint as calculated using nQuery Advisor software (Version 7). The primary efficacy analysis was intended to show superiority of RIPC in high-risk cardiac surgery patients, applying a two-sided $\chi^2$ test on significance level $\alpha=0.05$. The expected AKI rate in the control group treated with sham-RIPC was 50%. The expected absolute risk reduction for AKI was 18%. Resulting from these considerations and a power of 80%, the required sample size was calculated to be 117 evaluable patients per treatment group, i.e. 234 in total. An additional 12 patients were recruited in order to account for loss to follow-up or non-evaluable data.

The primary efficacy analysis included all randomized subjects (full analysis set) and was performed according to the intent-to-treat principle, i.e. all subjects were analysed according to their randomization. Descriptive statistics were summarized for categorical variables as frequency (%) and were compared between groups with $\chi^2$ test (or Fisher exact test if the produced matrixes contained cells with expected counts <5). Continuous variables, expressed as mean (SD), were compared between groups with an unpaired Student's t-test. Continuous variables, which were not distributed normally, were analyzed using nonparametric tests (Mann-Whitney U and Wilcoxon for unpaired and paired observations, respectively).

To identify the association between various risk factors and AKI, multivariable logistic regression (MVLR) was performed with AKI within 72 hours of surgery (yes or no) as the dependent variable. We included variables from the Cleveland Clinic Foundation score, (age, gender, diabetes, COPD, previous heart surgery, preoperative creatinine) along with HMGB-1, [TIMP-2]·[IGFBP7] (difference between pre- and post-RIPC) and RIPC as dependent variables using backward likelihood ratios for variable retention in the model. We used the Wald test and reported p-values odds ratios with 95% confidence intervals. To identify factors associated with [TIMP-2]·[IGFBP7] immediately after RIPC we used a pre-defined cut-off of 0.5 (ng/ml)$^2$/1000, and used MVLR with the same variables as described above (except [TIMP-2]·[IGFBP7]) as independent variables. Final model selection was based on AUC analysis. IBM SPSS version 21.0 software (IBM Corp. in Armonk, N.Y.) was used. Two-sided p values ≤0.05 were considered as indicative of statistical significance.

Example 6: Results

Primary outcome: Significantly fewer patients in the RIPC arm developed AKI within 72 h after surgery compared with the control group (37.5% vs 52.5%; p=0.02; RR, 0.76; 95% CI, 0.60 to 0.96; absolute risk reduction: 15.0%; 95% CI, xx to xx; relative risk reduction: 28.6%; 95% CI, xx to xx) (FIG. 1A and Table 2).

TABLE 2

Outcomes

| | Control (n = 120) | RIPC (n = 120) | p-value |
|---|---|---|---|
| Primary outcome | | | |
| AKI within 72 hrs [%] | 63 (52.5) | 45 (37.5) | 0.02 |
| Stage 1 [%] | 32 (26.7) | 30 (25) | |
| Stage 2 [%] | 14 (11.7) | 8 (6.7) | |
| Stage 3 [%] | 17 (14.2) | 7 (5.8) | |
| Secondary outcomes | | | |
| RRT [%] | 19 (15.8) | 7 (5.8) | 0.01 |
| Time on mechanical ventilation [h] | 15 (117) | 14 (48) | 0.16 |
| Intensive Care Unit stay [days] | 4 (8) | 3 (5) | 0.049 |
| Hospital stay [days] | 13 (13) | 12 (13) | 0.45 |
| In-hospital death [%] | 4 (3.3) | 6 (5.0) | 0.54 |
| 30-day mortality [%] | 5 (4.2) | 7 (5.8) | 0.77 |
| Myocardial infarction [%] | 5 (4.2) | 6 (5.0) | 0.76 |
| Stroke [%] | 3 (2.5) | 2 (1.7) | 0.65 |

RRT, renal replacement therapy.
Data are mean (SD) or number (%).
p ≤ 0.05 significant Secondary outcomes: RIPC significantly reduced the number of moderate and severe AKI cases compared to the control group (12.5% vs 25.8%; p=0.02; RR, 0.85; 95% CI, 0.75 to 0.97) (FIG. 1A), but did not reduce the rate of mild AKI (25% vs 26.7%; p=0.77; RR, 0.98; 95% CI, 0.84 to 1.14). Use of RRT and length of ICU stay were significantly reduced with RIPC (Table 2). However, we found no significant differences between groups in time on mechanical ventilation, myocardial infarction, and perioperative stroke (Table 2). Length of hospital stay after surgery was comparable (Table 2). The all-cause in-hospital death and 30-day mortality were not different between groups (Table 2).

Biomarker results: Baseline urinary [TIMP-2]·[IGFBP7] (calculated as the product of the individual concentrations) and NGAL concentrations, drawn immediately before the intervention, did not differ between groups (FIGS. 1B and 1C). Patients in the RIPC group exhibited an elevated urinary [TIMP-2]·[IGFBP7] concentration immediately after RIPC compared to the control group (FIG. 1B). By contrast, urinary NGAL concentrations did not increase at this time point in either group (FIG. 1C). After CPB, the RIPC group had significantly higher urinary [TIMP-2]·[IGFBP7] concentrations (4 h, and 12 h after CPB) compared to the control group (FIG. 1B). Urinary NGAL concentrations were significantly higher in the control group at 4 h after CPB but did not differ at other time points (FIG.

1C). High mobility group box protein-1 (HMGB-1), a damage associated molecular pattern (DAMP), was measured at baseline and after the intervention (before CPB). The urinary HMGB-1 concentration was similar in both groups at baseline. However, urinary HMGB-1 significantly increased immediately after RIPC (FIG. 1D).

Figure 2:
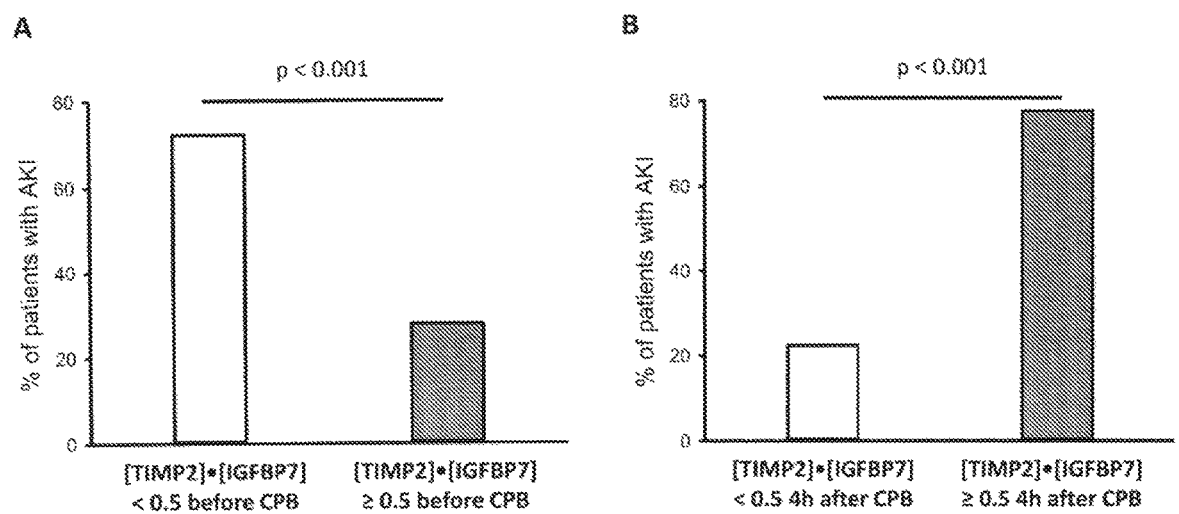
FIG. 2 depicts the percentage of patients with postoperative AKI stratified by urinary [TIMP-2]·[IGFBP7] concentration before (A) and 4 h after (B) CPB. CPB, cardiopulmonary bypass.

Patients with urinary [TIMP-2]·[IGFBP7] concentrations ≥0.5 $(ng/ml)^2/1000$ before the initiation of the CPB had a significantly reduced rate of AKI compared to patients with lower urinary [TIMP-2]·[IGFBP7] concentration (RR, 0.67; 95% CI, 0.53 to 0.83, p<0.001) (FIG. 2A). However, patients with urinary [TIMP-2]·[IGFBP7] concentrations ≥0.5 $(ng/ml)^2/1000$ four hours after CPB had a significantly increased rate of AKI compared to patients with lower urinary [TIMP-2]·[IGFBP7] concentration (RR, 2.99; 95% CI, 1.88 to 4.73, p<0.001) (FIG. 2B).

In MVLR analysis preoperative serum creatinine and previous heart surgery were associated with increased risk for AKI while post-RIPC HMGB-1 (OR, 0.75; 95% CI, 0.61 to 0.91; p=0.005) and [TIMP2]·[IGFBP7] (OR, 0.57; 95% CI, 0.35 to 0.94; p=0.03) were associated with lower risk for AKI (Table 3).

TABLE 3

Multivariable logistic regression analysis: AKI

| Variable | OR | 95% CI | Significance |
|---|---|---|---|
| Previous heart surgery [yes/no] | 2.25 | 0.94-5.40 | 0.04 |
| Preoperative Creatinine [mg/dl] | 2.29 | 1.11-4.71 | 0.03 |
| HMGB-1 after RIPC [(ng/ml)/100] | 0.75 | 0.61-0.91 | 0.005 |
| [TIMP2]•[IGFBP7] difference $[(ng/ml)^2/1000]^§$ | 0.57 | 0.35-0.94 | 0.03 |

§The [TIMP2]•[IGFBP7] value immediately after the intervention (before initiating cardiopulmonary bypass) minus the [TIMP2]•[IGFBP7] value before the intervention.
C-statistic (AUC): 0.718, CI: 0.65 to 0.78, p = 0.001.
OR, odds ratio; CI, confidence interval; p ≤ 0.05 significant.

Furthermore, both HMGB-1 and RIPC were highly significant predictors of post-RIPC [TIMP2]·[IGFBP7]≥0.5 $(ng/ml)^2/1000$ (Table 4).

TABLE 4

Multivariable logistic regression analysis:
[TIMP2]•[IGFBP7] ≥ 0.5

| Variable | OR | 95% CI | Significance |
|---|---|---|---|
| HMGB-1 after RIPC [(ng/ml)/100] | 1.20 | 1.02-1.41 | 0.032 |
| RIPC [yes/no] | 3.70 | 2.07-6.62 | 0.001 |

C-statistic (AUC): 0.62, CI: 0.55 to 0.69, p = 0.001.
OR, odds ratio; CI, confidence interval; p ≤ 0.05 significant.

AKI is closely associated with morbidity and mortality in the short and long terms. Several studies demonstrated an association between AKI and increased morbidity, short-term and long-term mortality, and use of resources in various patient populations. This relationship holds true even with small increases of serum creatinine for cardiac surgery patients. RIPC could thus represent a simple and promising strategy to provide protection to the kidney and improve outcomes. Such measures would be particularly desirable to deal with the increasingly challenging risk profiles of patients who are referred for cardiac surgery. Increases in urine [TIMP-2]·[IGFBP7] immediately after RIPC should therefore be protective from subsequent kidney injury induced by cardiac surgery, whereas as late increases in these markers (for example after CPB) should herald AKI. Our results fit this scenario exactly.

Example 7: References

1. Kellum J A, Lameire N, for KDIGO AKI Workgroup. Diagnosis, evaluation, and management of acute kidney injury: a KDIGO summary (Part 1). Critical care 2013; 17:204.
2. Thakar C V, Worley S, Arrigain S, Yared J P, Paganini E P. Improved survival in acute kidney injury after cardiac surgery. American journal of kidney diseases: the official journal of the National Kidney Foundation 2007; 50:703-11.
3. Baillot R G, Joanisse D R, Stevens L M, Doyle D P, Dionne B, Lellouche F. Recent evolution in demographic and clinical characteristics and in-hospital morbidity in patients undergoing coronary surgery. Can J Surg 2009; 52:394-400.
4. Chertow G M, Lazarus J M, Christiansen C L, et al. Preoperative renal risk stratification. Circulation 1997; 95:878-84.
5. Hobson C E, Yavas S, Segal M S, et al. Acute kidney injury is associated with increased long-term mortality after cardiothoracic surgery. Circulation 2009; 119:2444-53.
6. Rosner M H, Okusa M D. Acute kidney injury associated with cardiac surgery. Clinical journal of the American Society of Nephrology: CJASN 2006; 1:19-32.
7. Heusch G. Cardioprotection: chances and challenges of its translation to the clinic. Lancet 2013; 381:166-75.
8. Kharbanda R K, Nielsen T T, Redington A N. Translation of remote ischaemic preconditioning into clinical practice. Lancet 2009; 374:1557-65.
9. Przyklenk K, Bauer B, Ovize M, Kloner R A, Whittaker P. Regional ischemic 'preconditioning' protects remote virgin myocardium from subsequent sustained coronary occlusion. Circulation 1993; 87:893-9.
10. Domanski M J, Mahaffey K, Hasselblad V, et al. Association of myocardial enzyme elevation and survival following coronary artery bypass graft surgery. JAMA: the journal of the American Medical Association 2011; 305:585-91.
11. Cheung M M, Kharbanda R K, Konstantinov I E, et al. Randomized controlled trial of the effects of remote ischemic preconditioning on children undergoing cardiac surgery: first clinical application in humans. Journal of the American College of Cardiology 2006; 47:2277-82.
12. Zhou W, Zeng D, Chen R, et al. Limb ischemic preconditioning reduces heart and lung injury after an open heart operation in infants. Pediatric cardiology 2010; 31:22-9.
13. Thielmann M, Kottenberg E, Kleinbongard P, et al. Cardioprotective and prognostic effects of remote ischaemic preconditioning in patients undergoing coronary artery bypass surgery: a single-centre randomised, double-blind, controlled trial. Lancet 2013; 382:597-604.
14. Hausenloy D J, Mwamure P K, Venugopal V, et al. Effect of remote ischaemic preconditioning on myocardial injury in patients undergoing coronary artery bypass graft surgery: a randomised controlled trial. Lancet 2007; 370: 575-9.
15. Xie J J, Liao X L, Chen W G, et al. Remote ischaemic preconditioning reduces myocardial injury in patients undergoing heart valve surgery: randomised controlled trial. Heart 2012; 98:384-8.
16. Gassanov N, Nia A M, Caglayan E, Er F. Remote ischemic preconditioning and renoprotection: from myth to a novel therapeutic option? Journal of the American Society of Nephrology: JASN 2014; 25:216-24.

17. Crowley L E, McIntyre C W. Remote ischaemic conditioning-therapeutic opportunities in renal medicine. Nature reviews Nephrology 2013; 9:739-46.
18. Hausenloy D J, Yellon D M. Remote ischaemic preconditioning: underlying mechanisms and clinical application. Cardiovascular research 2008; 79:377-86.
19. Jaeschke H. Mechanisms of Liver Injury. II. Mechanisms of neutrophil-induced liver cell injury during hepatic ischemia-reperfusion and other acute inflammatory conditions. American journal of physiology Gastrointestinal and liver physiology 2006; 290:G1083-8.
20. Choi Y S, Shim J K, Kim J C, et al. Effect of remote ischemic preconditioning on renal dysfunction after complex valvular heart surgery: a randomized controlled trial. The Journal of thoracic and cardiovascular surgery 2011; 142:148-54.
21. Zimmerman R F, Ezeanuna P U, Kane J C, et al. Ischemic preconditioning at a remote site prevents acute kidney injury in patients following cardiac surgery. Kidney international 2011; 80:861-7.
22. Gallagher S M, Jones D A, Kapur A, et al. Remote ischemic preconditioning has a neutral effect on the incidence of kidney injury after coronary artery bypass graft surgery. Kidney international 2014.
23. Endre Z H. Renal ischemic preconditioning: finally some good news for prevention of acute kidney injury. Kidney international 2011; 80:796-8.
24. KDIGO AKI Work Group: KDIGO clinical practice guideline for acute kidney injury. Kidney international Supplement 2012; 2:1-138.
25. Thakar C V, Arrigain S, Worley S, Yared J P, Paganini E P. A clinical score to predict acute renal failure after cardiac surgery. Journal of the American Society of Nephrology: JASN 2005; 16:162-8.
26. Kottenberg E, Musiolik J, Thielmann M, Jakob H, Peters J, Heusch G. Interference of propofol with signal transducer and activator of transcription 5 activation and cardioprotection by remote ischemic preconditioning during coronary artery bypass grafting. The Journal of thoracic and cardiovascular surgery 2014; 147:376-82.
27. Kottenberg E, Thielmann M, Bergmann L, et al. Protection by remote ischemic preconditioning during coronary artery bypass graft surgery with isoflurane but not propofol—a clinical trial. Acta anaesthesiologica Scandinavica 2012; 56:30-8.
28. Murphy G S, Hessel E A, 2nd, Groom R C. Optimal perfusion during cardiopulmonary bypass: an evidence-based approach. Anesthesia and analgesia 2009; 108:1394-417.
29. Meersch M, Schmidt C, Van Aken H, et al. Urinary TIMP-2 and IGFBP7 as Early Biomarkers of Acute Kidney Injury and Renal Recovery following Cardiac Surgery. PloS one 2014; 9:e93460.
30. Venugopal V, Hausenloy D J, Ludman A, et al. Remote ischaemic preconditioning reduces myocardial injury in patients undergoing cardiac surgery with cold-blood cardioplegia: a randomised controlled trial. Heart 2009; 95:1567-71.
31. Hoole S P, Heck P M, Sharples L, et al. Cardiac Remote Ischaemic Preconditioning in Coronary Stenting (CRISP Stent) Study: a prospective, randomized control trial. Circulation 2009; 119:820-7.
32. Botker H E, Kharbanda R, Schmidt M R, et al. Remote ischaemic conditioning before hospital admission, as a complement to angioplasty, and effect on myocardial salvage in patients with acute myocardial infarction: a randomised trial. Lancet 2010; 375:727-34.
33. Ali Z A, Callaghan C J, Lim E, et al. Remote ischemic preconditioning reduces myocardial and renal injury after elective abdominal aortic aneurysm repair: a randomized controlled trial. Circulation 2007; 116:I98-105.
34. Venugopal V, Laing C M, Ludman A, Yellon D M, Hausenloy D. Effect of remote ischemic preconditioning on acute kidney injury in nondiabetic patients undergoing coronary artery bypass graft surgery: a secondary analysis of 2 small randomized trials. American journal of kidney diseases: the official journal of the National Kidney Foundation 2010; 56:1043-9.
35. Engler R L, Yellon D M. Sulfonylurea KATP blockade in type II diabetes and preconditioning in cardiovascular disease. Time for reconsideration. Circulation 1996; 94:2297-301.
36. Lee H T, Ota-Setlik A, Fu Y, Nasr S H, Emala C W. Differential protective effects of volatile anesthetics against renal ischemia-reperfusion injury in vivo. Anesthesiology 2004; 101:1313-24.
37. Piriou V, Chiari P, Lhuillier F, et al. Pharmacological preconditioning: comparison of desflurane, sevoflurane, isoflurane and halothane in rabbit myocardium. British journal of anaesthesia 2002; 89:486-91.
38. Schwartz Longacre L, Kloner R A, Arai A E, et al. New horizons in cardioprotection: recommendations from the 2010 National Heart, Lung, and Blood Institute Workshop. Circulation 2011; 124:1172-9.
39. Hausenloy D J, Erik Botker H, Condorelli G, et al. Translating cardioprotection for patient benefit: position paper from the Working Group of Cellular Biology of the Heart of the European Society of Cardiology. Cardiovascular research 2013; 98:7-27.
40. Gomez H, Ince C, De Backer D, et al. A unified theory of sepsis-induced acute kidney injury: inflammation, microcirculatory dysfunction, bioenergetics, and the tubular cell adaptation to injury. Shock 2014; 41:3-11.
41. Prowle J, Bagshaw S M, Bellomo R. Renal blood flow, fractional excretion of sodium and acute kidney injury: time for a new paradigm? Current opinion in critical care 2012; 18:585-92.
42. Bonventre J V, Yang L. Cellular pathophysiology of ischemic acute kidney injury. The Journal of clinical investigation 2011; 121:4210-21.
43. Kinsey G R, Sharma R, Okusa M D. Regulatory T cells in AKI. Journal of the American Society of Nephrology: JASN 2013; 24:1720-6.
44. Boonstra J, Post J A. Molecular events associated with reactive oxygen species and cell cycle progression in mammalian cells. Gene 2004; 337:1-13.
45. Devarajan P. Update on mechanisms of ischemic acute kidney injury. Journal of the American Society of Nephrology: JASN 2006; 17:1503-20.
46. Kashani K, Al-Khafaji A, Ardiles T, et al. Discovery and validation of cell cycle arrest biomarkers in human acute kidney injury. Critical care 2013; 17:R25.
47. Bihorac A, Chawla L S, Shaw A D, et al. Validation of Cell-Cycle Arrest Biomarkers for Acute Kidney Injury Using Clinical Adjudication. American journal of respiratory and critical care medicine 2014.
48. Yang Q H, Liu D W, Long Y, Liu H Z, Chai W Z, Wang X T. Acute renal failure during sepsis: potential role of cell cycle regulation. J Infect 2009; 58:459-64.
49. Rodier F, Campisi J, Bhaumik D. Two faces of p53: aging and tumor suppression. Nucleic Acids Res 2007; 35:7475-84.

50. Tsung A, Tohme S, Billiar T R. High mobility group box-1 in sterile inflammation. Journal of internal medicine 2014.
51. Wu H, Steenstra R, de Boer E C, et al. Preconditioning with recombinant high-mobility group box 1 protein protects the kidney against ischemia-reperfusion injury in mice. Kidney international 2014; 85:824-32.
52. Mangano C M, Diamondstone L S, Ramsay J G, Aggarwal A, Herskowitz A, Mangano D T. Renal dysfunction after myocardial revascularization: risk factors, adverse outcomes, and hospital resource utilization. The Multicenter Study of Perioperative Ischemia Research Group. Ann Intern Med 1998; 128:194-203.
53. Ryckwaert F, Boccara G, Frappier J M, Colson P H. Incidence, risk factors, and prognosis of a moderate increase in plasma creatinine early after cardiac surgery. Critical care medicine 2002; 30:1495-8.
54. Lassnigg A, Schmidlin D, Mouhieddine M, et al. Minimal changes of serum creatinine predict prognosis in patients after cardiothoracic surgery: a prospective cohort study. Journal of the American Society of Nephrology: JASN 2004; 15:1597-605.
55. Loef B G, Epema A H, Smilde T D, et al. Immediate postoperative renal function deterioration in cardiac surgical patients predicts in-hospital mortality and long-term survival. Journal of the American Society of Nephrology: JASN 2005; 16:195-200.
56. Dasta J F, Kane-Gill S L, Durtschi A J, Pathak D S, Kellum J A. Costs and outcomes of acute kidney injury (AKI) following cardiac surgery. Nephrology, dialysis, transplantation: official publication of the European Dialysis and Transplant Association—European Renal Association 2008; 23:1970-4.
57. Zappitelli M, Bernier P L, Saczkowski R S, et al. A small post-operative rise in serum creatinine predicts acute kidney injury in children undergoing cardiac surgery. Kidney international 2009; 76:885-92.
58. Parikh C R, Coca S G, Wang Y, Masoudi F A, Krumholz H M. Long-term prognosis of acute kidney injury after acute myocardial infarction. Archives of internal medicine 2008; 168:987-95.
59. Lafrance J P, Miller D R. Acute kidney injury associates with increased long-term mortality. Journal of the American Society of Nephrology: JASN 2010; 21:345-52.
60. Chertow G M, Burdick E, Honour M, Bonventre J V, Bates D W. Acute kidney injury, mortality, length of stay, and costs in hospitalized patients. Journal of the American Society of Nephrology: JASN 2005; 16:3365-70.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of preconditioning a subject for a therapeutic intervention comprising a cardiac or vascular surgery and testing the preconditioned subject, the method comprising:
    performing a remote ischemic preconditioning procedure on the subject; and
    performing a first assay and a second assay on a body fluid sample obtained from the subject after performing the remote ischemic preconditioning procedure,
        wherein the first assay measures an amount of Insulin-like growth factor-binding protein 7 (IGFBP7) in the sample and the second assay measures an amount of Tissue inhibitor of metalloproteinases 2 (TIMP2) in the sample, and
        wherein the first and second assays are performed prior to performance of the therapeutic intervention for which the subject was preconditioned.

2. The method of claim 1, wherein the therapeutic intervention comprises a heart valve repair/replacement, a percutaneous coronary intervention (PCI), a coronary artery bypass grafting, an aneurysm repair, an endovascular stent repair, or a cardiac surgery requiring cardiopulmonary bypass.

3. The method of claim 1, wherein the therapeutic intervention further comprises administration of one or more nephrotoxic agents.

4. The method of claim 3, wherein the one or more nephrotoxic agents comprises a radiocontrast agent, an antibiotic with nephrotoxic potential, a heavy metal preparation, a cancer chemotherapeutic agent, a nonsteroidal anti-inflammatory drug [NSAID], tacrolimus, an aminoglycoside, foscarnet, ethylene glycol, hemoglobin, myoglobin, ifosfamide, methotrexate, or streptozotocin.

5. The method of claim 1, wherein the remote ischemic preconditioning procedure comprises applying multiple cycles of a period of ischemia induced by inflating a blood-pressure cuff applied to the subject to at least 50 mmHg followed by a period of reperfusion.

6. The method of claim 1, further comprising combining a first assay result from the first assay and a second assay result from the second assay to provide a single composite value, wherein the single composite value is the product of multiplying the concentration of IGFBP7 and the concentration of TIMP2.

7. The method of claim 6, further comprising performing a second remote ischemic preconditioning procedure if the single composite value is below a predetermined threshold, wherein the predetermined threshold is about 0.5 $(ng/ml)^2/1000$.

8. The method of claim 7, further comprising performing a second remote ischemic preconditioning procedure if the single composite value is below a predetermined threshold, wherein the predetermined threshold is between about 0.3 $(ng/ml)^2/1000$ and about 3 $(ng/ml)^2/1000$.

9. The method of claim 7, further comprising performing a second remote ischemic preconditioning procedure if the single composite value is below a predetermined threshold, wherein the predetermined threshold is between about 0.5 $(ng/ml)^2/1000$ and about 2 $(ng/ml)^2/1000$.

10. The method of claim 6, further comprising performing the therapeutic intervention.

11. A method of testing a subject after treatment with a remote ischemic preconditioning procedure, the method comprising:
performing a first assay and a second assay on a body fluid sample obtained from the subject having received the remote ischemic preconditioning procedure,
wherein the first assay measures an amount of Insulin-like growth factor-binding protein 7 (IGFBP7) in the sample and the second assay measures an amount of Tissue inhibitor of metalloproteinases 2 (TIMP2) in the sample, and
wherein the first and second assay are performed after the remote ischemic preconditioning procedure had been performed on the subject and prior to performance of a therapeutic intervention for which the subject was preconditioned, wherein the therapeutic intervention comprises a cardiac or vascular surgery.

12. The method of claim 11, further comprising performing the therapeutic intervention.

13. The method of claim 12, wherein the therapeutic intervention comprises a heart valve repair/replacement, a percutaneous coronary intervention (PCI), a coronary artery bypass grafting, an aneurysm repair, an endovascular stent repair, or a cardiac surgery requiring cardiopulmonary bypass.

14. The method of claim 12, wherein the therapeutic intervention comprises a cardiac surgery requiring cardiopulmonary bypass.

15. The method of claim 11, wherein the therapeutic intervention further comprises administration of one or more nephrotoxic agents, wherein the one or more nephrotoxic agents comprises a radiocontrast agent, an antibiotic with nephrotoxic potential, a heavy metal preparation, a cancer chemotherapeutic agent, a nonsteroidal anti-inflammatory drug [NSAID], tacrolimus, an aminoglycoside, foscarnet, ethylene glycol, hemoglobin, myoglobin, ifosfamide, methotrexate, or streptozotocin.

16. The method of claim 11, the method further comprising multiplying a first assay result and a second assay result to produce single composite value, wherein the first assay result is a concentration of IGFBP7 and the second assay result is a concentration of TIMP2.

17. The method of claim 16, further comprising performing a second remote ischemic preconditioning procedure if the single composite value is below a predetermined threshold, wherein the predetermined threshold is about 0.5 $(ng/ml)^2/1000$.

18. The method of claim 16, further comprising performing a second remote ischemic preconditioning procedure if the single composite value is below a predetermined threshold, wherein the predetermined threshold is between about 0.3 $(ng/ml)^2/1000$ and about 3 $(ng/ml)^2/1000$.

19. The method of claim 16, further comprising performing a second remote ischemic preconditioning procedure if the single composite value is below a predetermined threshold, wherein the predetermined threshold is between about 0.5 $(ng/ml)^2/1000$ and about 2 $(ng/ml)^2/1000$.

20. The method of claim 12, further comprising performing the remote ischemic preconditioning procedure.

* * * * *

UNITED STATES PATENT AND TRADEMARK OFFICE
CERTIFICATE OF CORRECTION

Page 1 of 1

PATENT NO. : 11,243,202 B2
APPLICATION NO. : 15/565318
DATED : February 8, 2022
INVENTOR(S) : McPherson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
Twenty-ninth Day of November, 2022

Katherine Kelly Vidal
*Director of the United States Patent and Trademark Office*